US009662080B2

(12) United States Patent
Hwu et al.

(10) Patent No.: US 9,662,080 B2
(45) Date of Patent: May 30, 2017

(54) METHOD OF TRACKING SPECIFIC CELLS IN VIVO

(71) Applicant: ACADEMIA SINICA, Taipei (TW)

(72) Inventors: Yeu-Kuang Hwu, Taipei (TW); Chia-Chi Chien, Taipei (TW); Cheng-Liang Wang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 441 days.

(21) Appl. No.: 14/016,060

(22) Filed: Aug. 31, 2013

(65) Prior Publication Data

US 2014/0066762 A1 Mar. 6, 2014

(30) Foreign Application Priority Data

Aug. 31, 2012 (TW) .............................. 101131694 A

(51) Int. Cl.
| | | |
|---|---|---|
| *A61B 5/05* | (2006.01) | |
| *A61B 6/00* | (2006.01) | |
| *A61K 49/00* | (2006.01) | |
| *B82Y 5/00* | (2011.01) | |
| *B82Y 15/00* | (2011.01) | |

(52) U.S. Cl.
CPC .............. *A61B 6/485* (2013.01); *A61B 6/481* (2013.01); *A61B 6/508* (2013.01); *A61K 49/0065* (2013.01); *B82Y 5/00* (2013.01); *B82Y 15/00* (2013.01)

(58) Field of Classification Search
USPC ................................................ 600/407, 425
See application file for complete search history.

(56) References Cited

U.S. PATENT DOCUMENTS

2008/0102036 A1\* 5/2008 Poss et al. ...................... 424/9.6
2009/0137666 A1\* 5/2009 Wang ................... A61K 31/315
514/494

OTHER PUBLICATIONS

Chien et al., "X-Ray Imaging of Tumor Growth in Live Mice by Detecting Gold-Nanoparticle-Loaded Cells." Scientific Reports, published on Aug. 29, 2012. pp. 1-6.\*
Chien et al., "Synchrotron Mircoangiography Studies of Aniogensis in Mice with Microemulsions and Gold Nanoparticles." Anal. Bioanal. Chem., vol. 397, 2010. pp. 2109-2116.\*
Chien et al., "Complete Microscale Profiling of Tumor Microangiogensis: A Microradiological Methodology Reveals Fundamental Aspects of Tumor Angiogensis and Yields an Array of Quantitative Parameters for its Characterization." Biotechnology Advances, vol. 31, Available Online Dec. 14, 2011. pp. 396-401.\*
Dutly et al., "Fluorescent Microangiography (FMA): An Improved Tool to Visualize the Pulmonary Microvasculature." Laboratory Investigation, vol. 86, 2006. pp. 409-416.\*

(Continued)

*Primary Examiner* — James Kish
(74) *Attorney, Agent, or Firm* — PAI Patent & Trademark Law Firm; Chao-Chang David Pai

(57) ABSTRACT

A method of tracking specific cells in vivo is disclosed. The method of the disclosure includes: providing fluorescent nanoparticles suitable for targeting of specific cells; administering the fluorescent nanoparticles to a subject; providing an X-ray source to irradiate the subject; and determining the distribution and growth of the specific cells by the fluorescent images from the fluorescent nanoparticles and X-ray images of the subject irradiated by the X-ray source.

12 Claims, 2 Drawing Sheets

100

Providing a plurality of fluorescent nanoparticles suitable for targeting specific cells — Step 1

Administering the plurality of fluorescent nanoparticles to a subject — Step 2

Providing an X-ray source to irradiate the subject — Step 3

Determining the growth and distribution of the specific cells by fluorescent images of the plurality of fluorescent nanoparticles and the X-ray images from the subject irradiated by the X-ray source and observing the growth and distribution of a capillary in vivo by the X-ray images of the plurality of fluorescent nanoparticles — Step 4

(56) References Cited

OTHER PUBLICATIONS

Klasson, Anna. "MRI Contrast Enhancement using Gd2O3 Nanoparticles." 2008, Thesis paper, Linkoping University, pp. 1-52.*

Reddy et al., "Selective Toxicity of Zinc Oxide Nanoparticles to Prokaryotic and Ehkaryotic Systems." Applied Physics Letters 90, 2007, pp. 1-3.*

Wang et al, "Fluorescent Dye Encapsulated ZnO Particles with Cell-Specific Toxicity for Potential Use in Biomedical Applications." Journal of Material Sciences; 20; 2009, pp. 11-22.*

* cited by examiner

US 9,662,080 B2

METHOD OF TRACKING SPECIFIC CELLS IN VIVO

CROSS REFERENCE TO RELATED APPLICATIONS

This application claims priority of Taiwan Patent Application No. 101131694 filed on Aug. 31, 2012, the entirety of which is incorporated by reference herein.

BACKGROUND OF THE INVENTION

Field of the Invention

The present invention relates to a method of tracking cells in vivo, and in particular, relates to a method of tracking specific cells in vivo using fluorescent nanoparticles.

Description of the Related Art

In recent years, a variety of imaging methods have been developed for biological and medical applications. Especially, molecular imaging has been widely used to trace specific cells as a diagnosis tool for tumor cells treatments. There are many studies related to the application of fluorescent nanoparticles with luminescent properties to fluorescence imaging. In vivo small animal imaging, allows fluorescent images from fluorescent particles to be observed by a high-sensitivity camera; however, applications are limited as penetration of photons in tissue in vivo are often inadequate. Fluorescent particles that emit the near-infrared region (NIR) with high penetration are used for enhancement. Currently, small molecules of indocarbocyanine dyes are mainly used.

As the applications of fluorescent probes and fluorescent reporters become wider, fluorescent imaging has become an important analysis tool between basal and clinical researches. Although traditional small molecule near-infrared region (NIR) dyes are still used, development of fluorescent organic nanoparticles, fluorescent biological nanoparticles, and fluorescent inorganic nanoparticles for in vivo fluorescent imaging allow for the development of many powerful new tools for biological medical applications. Nanoparticles, as a platform, can be built up with multifunctional probes to be applied in multimodality imaging.

In view of this, a novel imaging method which can be combined with high-resolution and long life cycle fluorescent imaging, molecular targeting techniques, and X-ray imaging to function as a biomedical diagnosis tool is needed.

BRIEF SUMMARY OF THE INVENTION

A detailed description is given in the following embodiments with reference to the accompanying drawings.

In one embodiment, the present disclosure provides a method of tracking specific cells in vivo, which includes providing fluorescent nanoparticles suitable for targeting specific cells, administering the fluorescent nanoparticles to a subject, providing an X-ray source to irradiate the subject, and determining the growth and distribution of the specific cells by fluorescent images of the fluorescent nanoparticles and X-ray images from to the subject irradiated by the X-ray source and observing the growth and distribution of a capillary in vivo by X-ray images of the fluorescent nanoparticles.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
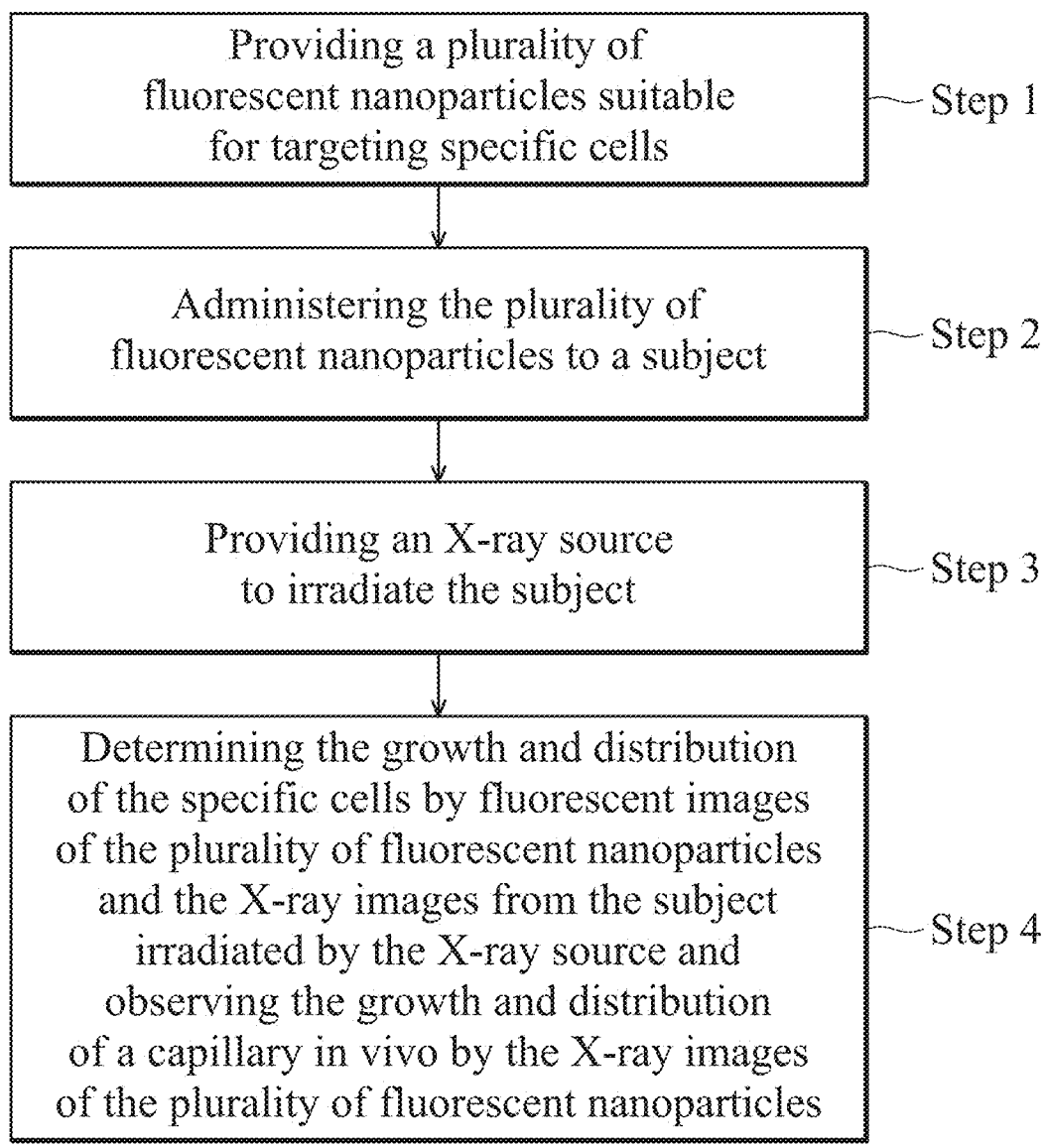
FIG. 1 shows the steps of the method according to one embodiment of the present application.

The following description is of the best-contemplated mode of carrying out the invention. This description is made for the purpose of illustrating the general principles of the invention and should not be taken in a limiting sense. The scope of the invention is best determined by reference to the appended claims. The present disclosure provides a method of tracking specific cells in vivo. Refer to FIG. 1. The method of tracking specific cells in vivo 100 includes administering fluorescent nanoparticles suitable for targeting specific cells to a subject (step 1 and step 2 of FIG. 1), wherein the fluorescent nanoparticles are capable of specifically targeting specific cells in vivo and being a contrast agent at the same time. Next, a high-coherent X-ray source is used to irradiate the subject (step 3 of FIG. 1), wherein the high-coherent X-ray source can stimulate the fluorescent nanoparticles in the subject to emit fluorescence. In some embodiments, the wavelength of fluorescence emitted by the fluorescent nanoparticles may be 450-900 nm. Then, the growth and distribution of the specific cells are determined by fluorescent images of the fluorescent nanoparticles in the subject and the X-ray images from the subject irradiated by the X-ray source (step 4 of FIG. 1).

In one embodiment, the fluorescent nanoparticles may be Gd-based nanoparticles, such as $Gd_2O_3$, or may include: $Y_3Al_5O_{12}$, $Y_2SiO_5$, ZnO, $BaMgAl_{14}O_{23}$, $Ti_2O_3$, $Zn_2SiO_2$, $Cn_2SiO_4$, $BaSiO_4$, or $(Y, Gd)BO_3$ nanoparticles, which may not only be stimulated by the X-ray source to emit fluorescence, but also function as biomedical probes to facilitate tracking of the distribution of the tumor cells in vivo. The above characteristics may be applied on photodynamic therapy as a powerful clinical diagnosis work. To achieve the purpose of tracking tumor cells or imaging tumor vasculature, the fluorescent nanoparticles may have a diameter from between about 1 nm and 100 μm to show the location of tumors.

In one embodiment, the X-ray source used to trace tumor cells in vivo may include a synchrotron radiation X-ray source, a medical X-ray source, or a laboratory X-ray source. In one embodiment, the X-ray source may have an intensity of about 4 keV-20 MeV. The absorbed dose of the X-ray source in the subject is less than about 4 Gy, preferably between about 0.1 and 1 Gy.

Due to the high coherent X-ray source (4 keV-20 MeV), photons can penetrate the body, the fluorescent nanoparticles administrated in the subject and marked on the tumor cells to emit fluorescence can be efficiently stimulated and the autofluorescence background to the fluorescent images can be reduced. In addition, when the dosage of the X-ray accumulated to a certain amount, the irradiation time of the X-ray source to the subject may be less than about 1 millisecond, preferably less than about 100 milliseconds. The effective penetration depth of the subject irradiated by the X-ray source may be about 30 cm from the surface to the deep tissue. Since the high-energy X-ray source adopted in the present disclosure has a high penetration ability in vivo, tumor cells in vivo may be monitored immediately by fluorescent and X-ray images of the present disclosure, instead of having to perform sample slicing from living subjects as conventional medical imaging requires.

The present disclosure is suitable for tracking any kinds of somatic cells in a subject, such as tumor cells, wherein the subject may include humans, mammals, birds, amphibians, reptiles, fish, insects, and/or other appropriate multicellular animals. In one embodiment, by combining X-ray images, such as vascular development, cell calibration, a combination thereof, or fluorescence images, the growth and distribution of the traced cells may be determined.

Further, the applications of the present disclosure on photodynamic therapy (PDT), including using the high-energy X-ray source of the present disclosure, are capable of penetrating into deep living tissues, efficiently stimulating the photo-sensitive drugs swallowed? by tumor cells and overcoming the traditional inadequate penetration of light source in living tissues. The fluorescent nanoparticles of the present disclosure may be an excellent vector for photosensitive drugs, and the fluorescent nanoparticles, such as Gd-based nanoparticles, may be applied on photodynamic therapy (PDT) to treat cancer after being stimulated by the X-ray source. Therefore, a real-time diagnosis and treatment of cancer may be achieved by combining the fluorescent and X-ray imaging systems of the present disclosure and photodynamic therapy (PDT).

In summary, in comparison to conventional biomedical imaging, the present disclosure has the following advantages: (1) reduces the interference of the autofluorescence background to the fluorescent images; and (2) provides immediate monitoring of tumor cells in living tissues by fluorescent and X-ray imaging of the present disclosure, instead of having to perform sample slicing from living subjects as conventional medical imaging requires.

EXAMPLES

Example 1: X-Ray Images of Tumor Vessel Proliferation In Vivo

The mice used in this example were BALB/c mice (purchased from National Laboratory Animal Center, Taiwan) fed by the Academia Sinica Institutional Animal Care and Committee (AS IACUC). All mice were housed in individual cages (five per cage) and kept at 24±2° C. with a humidity of 40%-70% and a 12-hour light/dark cycle.

Figure 2:
FIG. 2 is an X-ray image of tumor angiogenesis using $Gd_2O_3$ as a contrast agent.

4-5 week old mice were anesthetize by intramuscular injection of 10 µl of Zoletil 50 (50 mg/kg; Virbac Laboratories, Carros, France), and PE-08 was cathetered in the mice (about 20-25 g of weight). Then, 200 µl, 10 mg/mL of a contrast agent with $Gd_2O_3$ was injected from the femoral artery into the late-stage tumor (16-day) of the mice through the above PE-08 catheters (BB31695, Scientific Commodities, Inc.: 0.2 mm, O.D.: 0.36 mm), wherein the injection velocity of each group of a contrast agent was 1 µl/s. During the imaging process, mice were anesthetized under 1% isoflurene in oxygen. X-ray images were taken after 1 minute starting from the injection of the contrast agent from the femoral artery into the mice, and the exposure time was 100 milliseconds. FIG. 2 shows an X-ray image of tumor angiogenesis in vivo using $Gd_2O_3$ as a contrast agent, and the distribution of a capillary was clearly revealed by the contrast agent.

Example 2: Fluorescent Images In Vivo

The mice used in this example were BALB/c mice (purchased from National Laboratory Animal Center, Taiwan) fed by the Academia Sinica Institutional Animal Care and Committee (AS IACUC). All mice were housed in individual cages (five per cage) and kept at 24±2° C. with a humidity of 40%-70% and a 12-hour light/dark cycle.

4-5 week old mice were anesthetize by intramuscular injection of 10 µl of Zoletil 50 (50 mg/kg; Virbac Laboratories, Carros, France), and PE-08 was catheered in the mice (about 20-25 g of weight). Then, 200 µl, A 10 mg/mL of a contrast agent with $Gd_2O_3$ was injected from the femoral artery into the late-stage tumor (16-day) of the mice through the above PE-08 catheters (BB31695, Scientific Commodities, Inc.: 0.2 mm, O.D.: 0.36 mm), wherein the injection velocity of each group of the contrast agent was 1 µl/s. During the imaging process, mice were anesthetized under 1% isoflurene in oxygen. X-ray images were taken after 1 minute from injection of the contrast agent from the femoral artery into the mice, and the exposure time was 100 milliseconds.

Pictures of the mice sample with or without the X-ray irradiation were taken from some examples. In comparison to the imaging without irradiation, imaging with irradiation revealed orange spots at the tumor sites. The orange spots from the leg indicated $Gd_2O_3$ nanoparticles deposited at a tumor site via intra-arterial injection.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of tracking specific cells in vivo, comprising:
providing a plurality of fluorescent nanoparticles suitable for targeting specific cells;
administering the plurality of fluorescent nanoparticles to a subject, wherein the plurality of fluorescent nanoparticles comprises $Gd_2O_3$, $Y_3Al_5O_{12}$, $Y_2SiO_5$, ZnO, $BaMgAl_{14}O_{23}$, $Ti_2O_3$, $Zn_2SiO_2$, $Cn_2SiO_4$, $BaSiO_4$, or $(Y,Gd)BO_3$;
providing an X-ray source to irradiate the subject, wherein an X-ray image of the subject irradiated by the X-ray source is produced and the plurality of fluorescent nanoparticles are also stimulated by the X-ray source to emit fluorescence; and
determining the growth and distribution of the specific cells by the fluorescence emitted by the plurality of fluorescent nanoparticles in the subject irradiated by the X-ray source and observing the growth and distribution of a capillary in vivo by the X-ray image of the subject irradiated by the X-ray source, wherein in the X-ray image of the subject irradiated by the X-ray source, the distribution of the capillary is revealed by the plurality of fluorescent nanoparticles.

2. The method of tracking specific cells in vivo as claimed in claim 1, wherein the plurality of fluorescent nanoparticles have a diameter between about 1 nm and 100 µm.

3. The method of tracking specific cells in vivo as claimed in claim 1, wherein the X-ray source comprises a synchrotron radiation X-ray source, a medical X-ray source, or a laboratory X-ray source.

4. The method of tracking specific cells in vivo as claimed in claim 3, wherein a photon energy of the X-ray source is between about 4 keV and 20 MeV.

5. The method of tracking specific cells in vivo as claimed in claim 1, wherein the absorbed dose of the X-ray source in the subject is less than about 100 Gy.

6. The method of tracking specific cells in vivo as claimed in claim 1, wherein the absorbed dose of the X-ray in the subject is between about 1 Gy and 30 Gy.

7. The method of tracking specific cells in vivo as claimed in claim 1, wherein the irradiation time of the X-ray source to the subject is less than about 30 minutes.

8. The method of tracking specific cells in vivo as claimed in claim 1, wherein the irradiation time of the X-ray to the subject is between about 100 milliseconds and 5 minutes.

9. The method of tracking specific cells in vivo as claimed in claim 1, wherein the subject comprises humans, mammals, birds, amphibians, reptiles, fish, insects, or other appropriate multicellular animals.

10. The method of tracking specific cells in vivo as claimed in claim 1, wherein the specific cells comprise tumor cells, stem cells, blood cells, tissue cells, or other appropriate somatic cells.

11. The method of tracking specific cells in vivo as claimed in claim 1, wherein the X-ray image comprises vascular development or cell targeting.

12. The method of tracking specific cells in vivo as claimed in claim 1, wherein the effective penetration depth of the subject irradiated by the X-ray source is about 30 cm from the surface to the deep tissue.

\* \* \* \* \*